United States Patent [19]

Damato

[11] Patent Number: 4,737,024

[45] Date of Patent: Apr. 12, 1988

[54] PERIMETRIC METHOD AND APPARATUS

[75] Inventor: Bertil E. Damato, Glasgow, Scotland

[73] Assignee: The University Court of the University of Glasgow, Scotland

[21] Appl. No.: 742,116

[22] Filed: Jun. 5, 1985

[30] Foreign Application Priority Data

Jun. 5, 1984 [GB] United Kingdom ............... 8414358
Apr. 16, 1985 [GB] United Kingdom ............... 8509741

[51] Int. Cl.⁴ .............................................. A61B 3/02
[52] U.S. Cl. .................................................. 351/224
[58] Field of Search ............... 351/224, 225, 226, 223, 351/246

[56] References Cited

FOREIGN PATENT DOCUMENTS 2454387 5/1976 Fed. Rep. of Germany ...... 351/226
772526 10/1980 U.S.S.R. ............................. 351/226

Primary Examiner—Rodney B. Bovernick
Attorney, Agent, or Firm—Stephen G. Rudisill

[57] ABSTRACT

The present invention provides an oculo-perimetric device for use in measuring the field of vision of a subject and comprises an extended area visual target 1 having a large plurality of generally regularly, angularly and/or radially, spaced apart individual target elements 2, disposed around a central reference target element 3 across substantially the whole of the area within a predetermined radial separation R from said reference target 3. The individual target elements 2 are provided with sequence indicating means 4 formed and arranged so as to define a visually discernible predetermined sequence for fixing of a subject's eye 5 on successive adjacent individual target elements 2. The central reference target element 3 is formed and arranged so as to be visually more prominent than the individual target elements 2.

15 Claims, 1 Drawing Sheet

U.S. Patent
Apr. 12, 1988
4,737,024
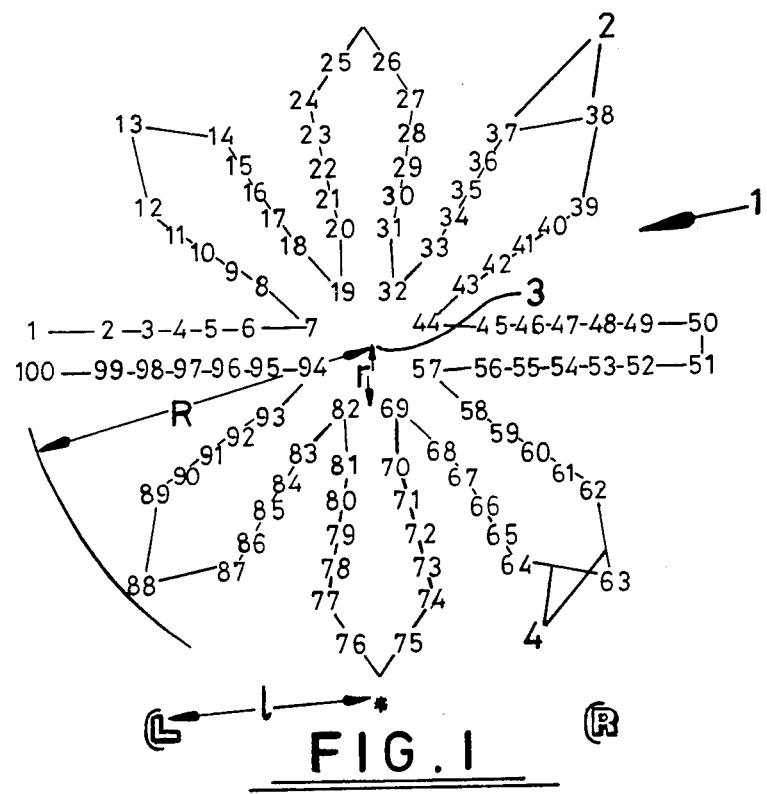
FIG. 1
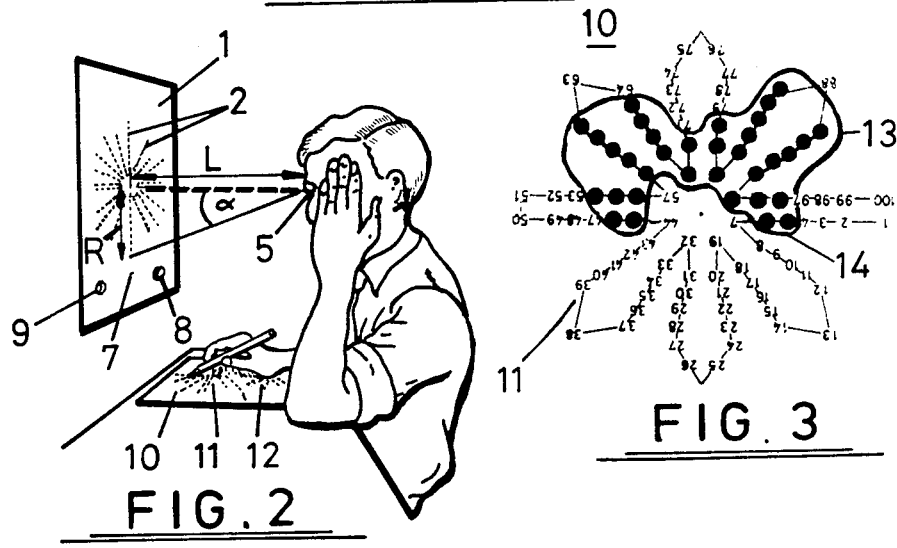
FIG. 2
FIG. 3

PERIMETRIC METHOD AND APPARATUS

The present invention relates to ocular perimetry and in particular to a device for use in ocular perimetry and a method using said device.

Conventionally ocular perimetric methods for use in the diagnosis and management of diseases of the eyes and brain (e.g. glaucoma, retinitis pigmentosa, tumours etc), are based on the use of a mobile optical target element around a central reference target element. The subject's eye is fixed on the reference target while the mobile target element is moved around it and any points at which the subject is unable to see the mobile target while still fixing his eye on the reference target, are recorded. These methods however suffer from a number of serious disadvantages. In the first place it is very difficult for the subject to maintain his eye in fixed alignment on the target and any deviation results in innaccuracies of measurement. Accordingly it is necessary for an operator to monitor the subject to identify any deviations of the eye as well as recording the results of the subjects response at different positions of the mobile target. Furthermore the conventional apparatus with the mobile target element, generally in the form of flashing lights, is very expensive.

It is an object of the present invention to avoid or minimize one or more of the above disadvantages.

The present invention provides an oculo-perimetric device for use in measuring the field of vision of a subject which device comprises an extended area visual target having a large plurality of generally regularly, angularly and/or radially, spaced apart individual target elements disposed around a central reference target element across substantially the whole of the area within a predetermined radial separation from said reference target, said individual target elements being provided with sequence indicating means formed and arranged so as to define a visually discernible predetermined sequence for fixing of an eye of the subject, in use of the device, on successive adjacent individual target elements, said central reference target element being formed and arranged so as to be visually more prominent than said individual target elements.

In a further aspect the present invention provides a method of measuring the field of vision of a subject comprising the steps of providing an oculo-perimetric device of the invention, supporting said device at a predetermined distance from an eye of said subject of not more than 3 times said predetermined radial separation, facing an eye of the subject to be tested, shading any other eye of the subject, and recording any of said individual target elements within said predetermined sequence of observation thereof at which individual target element said subject is unable to see said reference target when said eye is fixed on said individual target element.

Thus with the device and method of the present invention it is possible to obtain a good measurement of the central part of the field of vision of a subject i.e. that part subtending an angle of the order of 20° to 25° either side of the central axis in the field of view of the eye along which the eye is directed, in a simple and quick manner which at the same time is very much more economical than previously known systems for ocular perimetry.

Further preferred features and advantages of the invention will appear from the following detailed description given by way of example of a preferred embodiment illustrated with reference to the accompanying drawings in which:

FIG. 1 shows a device of the invention;

FIG. 2 is a schematic perspective view of the device of FIG. 1 in use in a method of the invention; and FIG. 3 shows part of a completed record sheet obtained in the method of FIG. 2.

FIG. 1 shows an oculo-perimetric device of the invention comprising a visual target in the form of a card 1 having printed thereon against a pale unsaturated colour background, in a pale unsaturated colour such as light blue, light green or pink, a plurality of individual target elements 2 around a central reference target 3 which is a dark saturated colour, usually black, so as to be substantially more visually prominent than the reduced visibility individual target elements 2. This helps to reduce confusion between the individual target elements 2 and the central reference target 3. As may be seen in the drawing the individual target elements 2 are more or less regularly spaced angularly around the reference target 3 and radially therefrom so as to substantially occupy the whole of the area within a predetermined radial separation R from the central reference target 3.

Conveniently the central test target is in the form of a series of faint concentric circles which may be filled in with black ink prior to the commencement of the test as required depending upon the size of central test target required by the subjects visual ability.

The individual target elements 2 are in the form of a sequence of numbers running from 1 to 100 with lines 4 interconnecting successive numbers which are disposed adjacently. In this way there is defined a predetermined sequence of the individual target elements 2 which can be followed by the subject's eye 5 (see FIG. 2). The interconnecting lines assist the subject, especially an illiterate one, in following a predetermined sequence through the individual target elements. The use of target elements in the form of numbers, or alternatively alphabetical characters aids in rapid and certain identification of the individual portions of the subject's field of view being tested at any given moment. On the one hand this facilitates recording of the results of the measurement and on the other hand also facilitates transmission and further processing of the data obtained through telephone and/or computer apparatus.

As shown in FIG. 2 the target card 1 is supported at a distance L from the subject's eye 5 such that the radius R of the area filled by the target elements 2 subtends an angle $\alpha$ of about 20° to 25° at the eye. Thus for example a card having a radius R of 45 cm would conveniently be supported at a distance L of 100 cm from the subject's eye. Conveniently the card includes at its base 6 distance setting means in the form of an eye fixing spot 7 and right and left eye targets 8 and 9 respectively, separated therefrom at a distance such that when the card is held at the distance L from the left eye which is fixed on the eye fixing spot 7 the left eye target 9 coincides with that eye's blind spot and thus cannot be seen. For the purposes o reproducibility and comparison it is clearly desirable that the card should be supported at the same relative distance for every test so that any given individual target element always corresponds to the same part of the eye's field of vision.

The test is carried out in a well lit environment and repeated under the same conditions. One eye is tested at a time while the other is occluded. As the subject reads these numbers in numerical order the movement of the eye induces a relative centripetal displacement of the central target in the visual field. Defects in the visual field are plotted by noting the numbers which are associated with disappearance of the central target. Conveniently these are plotted on a record sheet bearing a reduced size representation of the target.

The results are interpreted by a trained individual. To compare the result with one obtained by conventional techniques the completed record sheet is inverted. The presence and position of the normal blind spot on the record sheet provides a guide to the reliability of the patient's responses. The position of the blind spot (distance from the central reference target) will also indicate whether the test was carried out at the correct working distance or not.

For the purposes of self assessment, to which the present invention is particularly and uniquely well suited, a smaller size of target card with a radius R of 15 cm and a viewing distance L of 33 cm which can be used without glasses is generally more convenient.

It will of course be appreciated that the above device can be modified in various ways without departing from the scope of the present invention. In particular various other sequences of individual targets could be used including for example spiral arrangements. In the case of the individual target elements arrangement illustrated it will be noted that the generally 8-corner star shaped arrangement has an angular separation (around the central reference target) of the order of 25° in most cases. This illustrated arrangement has been found particularly convenient for maximising the detection of arcuate, quadrantic, hernianopic, and altitudinal visual field defects as well as a nasal step. Desirably, the sequence is arranged on the target so that a fairly early section e.g., numbers 2 to 4 in the above card are disposed in the region of the subject's blind spot. This helps to provide an early indication of the subject following the test procedure correctly.

Other modifications may also be made to the form of the target. Thus, for example, other colours could be used e.g., a black background with a white central target 3 and red individual target elements. Desirably an annular area around the central target 3 having a radius r subtending an angle of the order of 5° is left clear as shown in FIG. 1 in order to aid observation of this target 3. Other forms of visual target could also be used including representations of a card as illustrated and described above by optical and/or electronic means for example by projection of a transparency or display on a VDU such as a cathode ray tube, LCD or electrochemiluminescent display device. Also if assessment of a greater part of the field of vision than the abovementioned central part is required, then a concave target with a larger radius R could be employed extending up to angles α of the order of 70° or even 90° for a given viewing distance L.

Where an electronic display means is utilized the device may conveniently be formed and arranged so that the individual target elements 2 are individually transiently generated in said predetermined sequence.

Where an optical display means is used this is conveniently in the form of a set of coloured slides each with a different central target for viewing with a matching conventional hand held viewer or with a conventional slide projector. In one embodiment one slide is conveniently provided without a central target so that it can be placed in a suitable conventional stereoscopic viewer before the normal eye to enable the other eye to be tested with one of the other test slides. This particular embodiment allows individuals with uniocular central field defects to test their own field using this invention. Naturally a similar test procedure can be carried out using a pair of printed cards which are compatible with existing stereoscopes described hereinabove.

EXAMPLE

Method of detecting hidden field of vision defects.

The method is carried out using a self-assessment test card 1 as described above together with a record sheet 10 (see FIG. 2) on which are displayed two reduced size representations 11, 12 for use in recording the results of the test procedure for respective ones of the subject's eyes 5. The test procedure is carried out in accordance with the following instructions:

(i) Place the chart on a flat surface in a well lit room so that its centre is at eye level 33 cms from your face.

(ii) Test the right eye first. Keep the other eye completely covered throughout the procedure.

(iii) To check your position look down at the star below. If you are testing the right eye the letter R should disappear. If the left eye is being tested the letter L should disappear.

(iv) Look at a number on the chart. WITHOUT TAKING YOUR EYE OFF THAT NUMBER ask yourself whether you can still see the central black spot out of the corner of your eye. Do this with each number from 1 to 100, taking at least one second per number.

(v) The numbers which are associated with disappearance of the central spot should be circled on the record sheet.

(vi) Repeat the procedure with your other eye.

Results

FIG. 3 shows part of a record sheet obtained by the above method showing the results for one of the subject's eyes. A substantial visual defect area 13 may be seen extending from the blind spot area 14.

What is claimed is:

1. A method of measuring the field of vision of a subject comprising the steps of providing an extended area visual target having a large plurality of generally regularly, angularly and/or radially, spaced apart individual target elements disposed around a central reference target element across substantially the whole of the area within a predetermined radial separation from said reference target element, said individual target elements being provided with sequence indicating means formed and arranged so as to define a visually discernible predetermined sequence for fixing of an eye of the subject, in use of the device, on successive adjacent individual target elements; presenting said target at a predetermined distance from an eye of said subject of up to 3 times said predetermined radial separation, facing an eye of the subject to be tested; occluding any other eye of the subject; and recording any of said individual target elements within said predetermined sequence of observation thereof at which individual target element said subject is unable to see said reference target when said eye is fixed on said individual target element.

2. The method of claim 1 which includes the steps of providing distance determining means in the form of left and right hand indicia at a predetermined distance either side of a reference index on said target such that when said reference index is observed with one eye at a predetermined distance from said target such that the predetermined radial separation defining the area substantially occupied by the individual target elements subtends an angle at the eye of from 20° to 30°, the respective one of said left and right hand indicia corresponds with the blind spot of said eye; and moving at least one of said target and subject towards and/or away from the other until the respective one of said left and right hand indicia coincides with the blind spot of said eye and cannot be seen by said eye when said eye is fixed on the reference index.

3. The method of claim 1 which includes the step of generating said target on at least one of an electronic and an optical display means.

4. The method of claim 3 which includes the steps of individually transiently generating said individual target elements in said predetermined sequence.

5. An oculo-perimetric device for use in measuring the field of vision of a subject which device comprises an extended area visual target having a large plurality of generally regularly, angularly spaced apart individually, discrete localized target elements disposed around a central reference target element at a plurality of different angular and radial positions relative to said central reference target, across substantially the whole of the area within a predetermined radial separation from said reference target element, said individual target elements being provided with sequence indicating means formed and arranged so as to define a visually discernible predetermined sequence for fixing of an eye of the subject, in use of the device, on successive adjacent individual target elements, said central reference target element being formed and arranged so as to be visually more prominent than said individual target elements, said individual target elements are of a pale unsaturated colour whilst said central reference target is of a dark saturated colour; said individual target elements are in the form of a series of consecutive numbers constituting sequence indicating means; the sequence indicating means includes lines extending between successive adjacent individual target elements, further including observation distance determining means in the form of left and right hand indicia at a predetermined distance either side of a reference index such that when said reference index is observed with one eye at a predetermined distance from said target such that the predetermined radial separation defining the area substantially occupied by the individual target elements subtends an angle at the eye of from 20° to 30°, the respective one of said left and right indicia corresponds with the blind spot of said eye.

6. The device of claim 5 wherein said individual target elements are of a pale unsaturated colour whilst said central reference target is of a dark saturated colour.

7. The device of claim 6 wherein said individual target elements are in the form of a series of consecutive numbers constituting sequence indicating means.

8. The device of claim 7 wherein the sequence indicating means includes lines extending between successive adjacent individual target elements.

9. The device of claim 8 which includes observation distance determining means in the form of left and right hand indicia at a predetermined distance either side of a reference index such that when said reference index is observed with one eye at a predetermined distance from said target such that the predetermined radial separation defining the area substantially occupied by the individual target elements subtends an angle at the eye of from 20° to 30°, the respective one of said left and right indicia corresponds with the blind spot of said eye.

10. The device of claim 9 wherein said target is in the form of a planar medium with permanent markings thereon.

11. The device of claim 1 wherein said target comprises an electronic and/or optical display screen with said individual and central reference target elements electronically and/or optically generated and displayed thereon.

12. The device of claim 11 which device is formed and arranged so that said individual target elements are individually transiently generated in said predetermined sequence.

13. The device of claim 5 wherein each said individual target element is provided with a unique sequence indicating means thereby constituting an individual target element identification means therefor, thereby to facilitate accurate recording of determinations carried out using said device.

14. The device of claim 5 wherein said sequence indicating means are formed and arranged so as to define a generally starshaped pathway having eight limbs and extending across substantially the whole of said area within said predetermined radial separation.

15. An oculo-perimetric device for use in measuring the field of vision of a subject which device comprises an extended area visual target having a large plurality of generally regularly, angularly spaced apart individually, discrete localized target elements disposed around a central reference target element at a plurality of different angular and radial positions relative to said central reference target, across substantially the whole of the area within a predetermined radial separation from said reference target element, said individual target elements being provided with sequence indicating means formed and arranged so as to define a visually discernible predetermined sequence for fixing of an eye of the subject, in use of the device, on successive adjacent individual target elements, said central reference target element being formed and arranged so as to be visually more prominent than said individual target elements; wherein said sequence indicating means are formed and arranged so as to define a generally starshaped pathway having eight limbs and extending across substantially the whole of said area within said predetermined radial separation.

* * * * *